US008814872B2

(12) United States Patent
Bickenbach (10) Patent No.: US 8,814,872 B2
(45) Date of Patent: Aug. 26, 2014

(54) DOUBLE ROW KEEL CUT SAW BLADE

(75) Inventor: Christine A. Bickenbach, Naples, FL (US)

(73) Assignee: Arthrex, Inc., Naples, FL (US)

( * ) Notice: Subject to any disclaimer, the term of this patent is extended or adjusted under 35 U.S.C. 154(b) by 145 days.

(21) Appl. No.: 13/038,566

(22) Filed: Mar. 2, 2011

(65) Prior Publication Data

US 2011/0230887 A1    Sep. 22, 2011

Related U.S. Application Data

(60) Provisional application No. 61/314,482, filed on Mar. 16, 2010.

(51) Int. Cl.
*A61B 17/14* (2006.01)
*B23D 61/18* (2006.01)

(52) U.S. Cl.
USPC .............. 606/82; 606/178; 30/503; 30/503.5; 83/848

(58) Field of Classification Search
USPC ................ 606/79–85, 167, 176, 171, 177; 30/166.3, 392, 501, 502, 503, 503.5, 30/393, 394; 83/835–855; 452/135, 138, 452/139, 148, 149, 1–6, 13, 7, 102, 103; 144/218–240, 241
See application file for complete search history.

(56) References Cited

U.S. PATENT DOCUMENTS

| 1,455,621 | A | * | 5/1923 | Joyner | 30/166.3 |
| 3,905,374 | A | * | 9/1975 | Winter | 606/178 |
| 4,979,305 | A | * | 12/1990 | Leini | 30/369 |
| 6,050,163 | A | * | 4/2000 | Gravely et al. | 83/22 |
| 7,322,985 | B2 | * | 1/2008 | Lee | 606/71 |
| 8,206,392 | B2 | * | 6/2012 | Fisher et al. | 606/82 |
| 2001/0015120 | A1 | * | 8/2001 | Hickey | 83/661 |
| 2009/0044679 | A1 | * | 2/2009 | Souza et al. | 83/848 |
| 2011/0092975 | A1 | * | 4/2011 | Fisher et al. | 606/82 |

FOREIGN PATENT DOCUMENTS

WO    WO 2008014258 A2 * 1/2008 ............. A61F 2/44

OTHER PUBLICATIONS

"The Oxford Partial Knee", Surgical Technique, Fig. 39, Biomet (2009).
"Vanguard M Partial Knee", Lateral and Medial Surgical Technique, Figs. 34 and 80, Biomet (2009).

* cited by examiner

*Primary Examiner* — Todd Manahan
*Assistant Examiner* — Marcela I Shirsat
(74) *Attorney, Agent, or Firm* — Dickstein Shapiro LLP (57) ABSTRACT

A saw blade provided with two walls set apart from each other and with blade teeth arranged on each wall in a pattern along the distal end of each wall and on the inner surface of each wall. During a single cutting motion, the distal teeth provide the initial cut and the inner teeth remove additional material along the pathway. This increases the amount of material removed in one cut, leaving a small amount of material (bone) at the bottom of the slot for the surgeon to remove in the final step. Thus, the blade configuration and the tooth pattern of the saw blade improves the cutting efficiency.

18 Claims, 7 Drawing Sheets

DOUBLE ROW KEEL CUT SAW BLADE

CROSS-REFERENCE TO RELATED APPLICATIONS

This application claims the benefit of U.S. Provisional Application No. 61/314,482, filed Mar. 16, 2010, the entire disclosure of which is incorporated by reference herein.

FIELD OF THE INVENTION

The present invention relates to surgical saw blades and, more particularly, to a surgical saw blade that efficiently cuts a slot into the bone against which the blade is applied.

BACKGROUND OF THE INVENTION

In a surgical procedure, it is sometimes necessary to use a saw to remove tissue, including bone and cartilage. Often a powered saw is used to perform this procedure. A saw blade is attached to the saw. A drive assembly internal to the saw reciprocates the blade in a back and forth motion. This type of blade is provided with teeth that extend outwardly from a side edge of the blade body.

Figure 1:
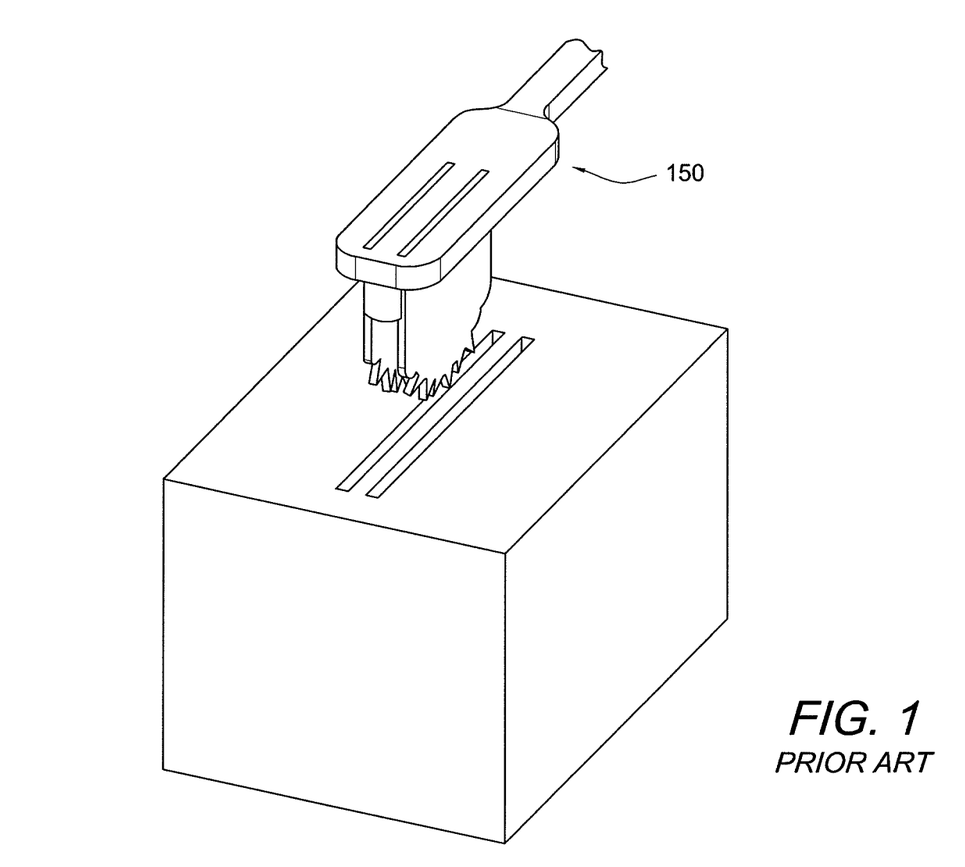
FIG. 1 illustrates a view of a prior art saw blade and the cut it makes.

FIG. 1 illustrates a surgical saw blade 150 and the cut created by the blade as is known in the prior art. As shown in FIG. 1, a wall of bone remains between the two cuts created by the blade of the prior art. The surgeon must remove the wall of bone using another instrument to create the desired slot.

SUMMARY OF THE INVENTION

The reciprocating saw blade of this invention is designed with two walls set apart from each other with blade teeth arranged on each wall in a pattern along the distal end of each wall and on the inner surface of each wall. An advantage of the patterned relationship of the blade teeth of this invention is that, during a single cutting motion, the distal teeth provide the initial cut and the inner teeth remove additional material along the pathway. This increases the amount of material removed in one cut, leaving a small amount of material (bone) at the bottom of the slot for the surgeon to remove in the final step. Thus, the blade configuration and the tooth pattern of the saw blade of this invention improves the cutting efficiency.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides a reciprocating saw blade which is designed with two walls set apart from each other with blade teeth arranged on each wall in a pattern along the distal end of each wall and on the inner surface of each wall. An advantage of the patterned relationship of the blade teeth of this invention is that, during a single cutting motion, the distal teeth provide the initial cut and the inner teeth remove additional material along the pathway. This increases the amount of material removed in one cut, leaving a small amount of material (bone) at the bottom of the slot for the surgeon to remove in the final step. Thus, the blade configuration and the tooth pattern of the saw blade of this invention improves the cutting efficiency.

Figure 2:
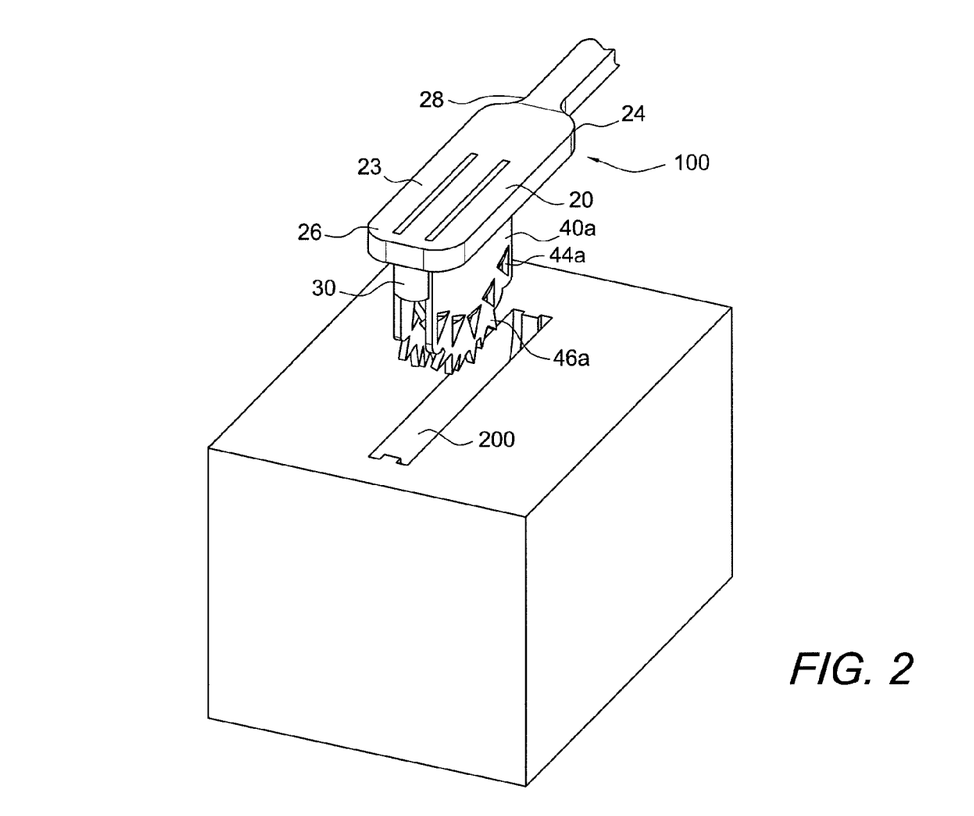
FIG. 2 is a view of the saw blade of the present invention and the cut it makes.

Referring now to the drawings, where like elements are designated by like reference numerals, FIG. 2 illustrates a surgical saw blade 100 constructed in accordance with the present invention. As shown in FIG. 2, saw blade 100 creates a slot 200 with minimal excess bone needing to be removed by the surgeon. Saw blade 100 has a base 20, a pair of opposing sidewalls 40a, 40b, a shaft 28 and a spacer 30. Teeth 46a, 46b extend from the distal end of the opposing sidewalls 40a, 40b and teeth 44a, 44b project from the inner surface of the sidewalls 40a, 40b. Saw blade 100 may be formed of material such as stainless steel and/or carbide. In an alternate embodiment, and as detailed below, there may be a third sidewall 40c with teeth inserted between the opposing sidewalls, 40a, 40b so the kerfs overlap.

Figure 3A:
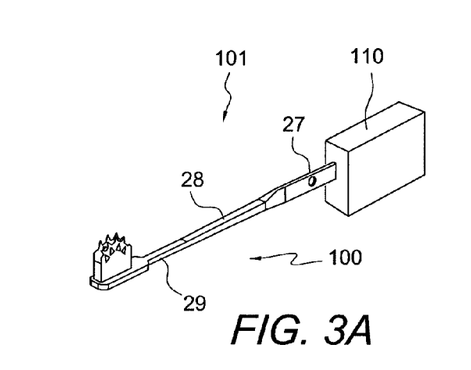
FIG. 3A illustrates a perspective view of a saw blade assembly of the present invention with the saw blade of FIG. 2.
Figure 3B:
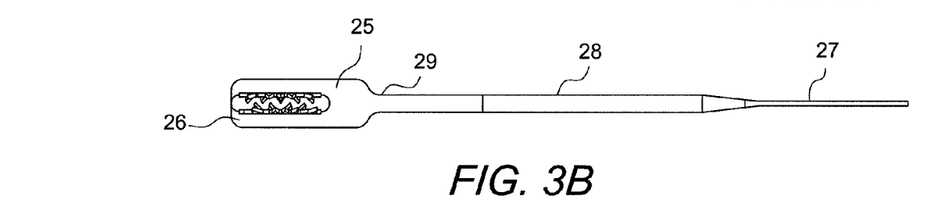
FIG. 3B illustrates a top view of the saw blade of FIG. 3A.
Figure 3C:
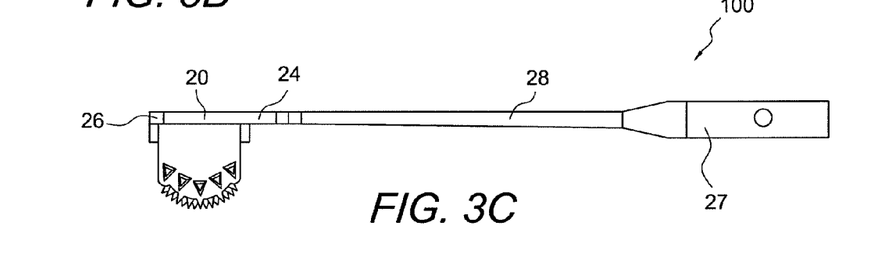
FIG. 3C illustrates a side view of the saw blade of FIG. 3A.
Figure 4A:
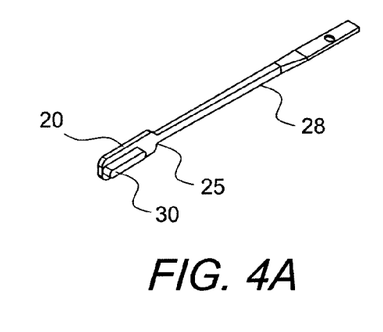
FIGS. 4A and 4B illustrate perspective views of the base of the saw blade of FIG. 2.
Figure 4B:
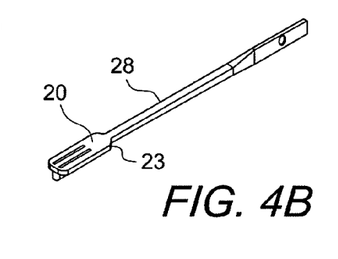
Figure 4C:
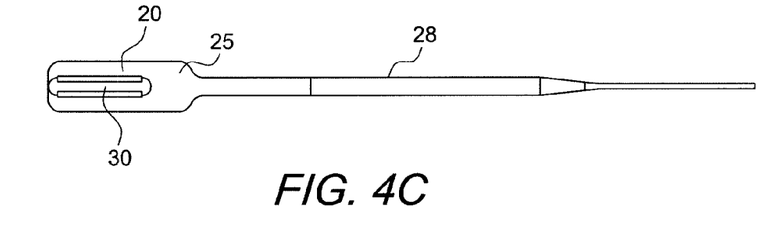
FIG. 4C illustrates a bottom view of the saw blade of FIG. 2.
Figure 4D:
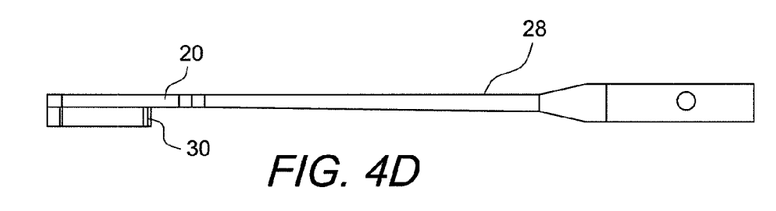
FIG. 4D illustrates a side view of the saw blade of FIG. 2.
Figure 4E:
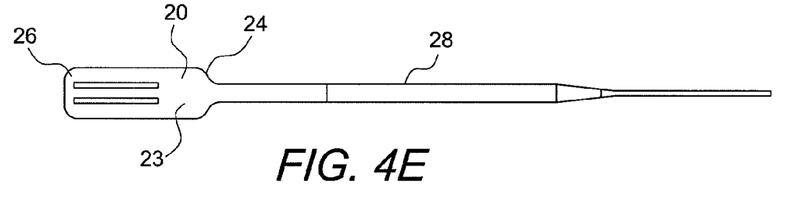
FIG. 4E illustrates a top view of the saw blade of FIG. 2.

Reference is now made to FIG. 3A which illustrates a saw blade assembly 101 that includes the saw blade 100 with a base 20 having a generally oblong shape with a proximal end 24 and a distal end 26 (FIGS. 3B and 3C). A shaft 28 extends from the proximal end of the base 20. Shaft 28 has a proximal end 27 and a distal end 29. Proximal end 27 is configured to connect to a drive assembly 110 of the saw (shown schematically in FIG. 3A). Proximal end 27 may have any configuration as is known in the art for connecting to a drive assembly.

As shown in FIGS. 4A-E, base 20 has a top surface 23 and a bottom surface 25. A spacer 30 is formed on the bottom surface 25 of the base. The spacer 30 is sized to reflect the desired width of the cut to be made by the saw blade 100. Additionally, the spacer 30 acts as a stop for determining the depth of the cut. A pair of side walls 40a, 40b extends from the bottom surface 25 of the base 20. Each side wall 40a, 40b has a center 41a, 41b, a periphery 49a, 49b, and two opposing side surfaces, for example, an inner surface 42a, 42b and an opposing outer surface 43a, 43b).

Figure 5A:
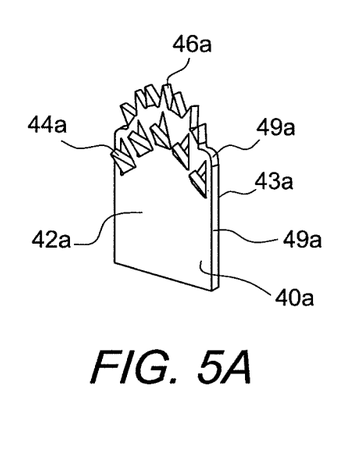
FIGS. 5A-C illustrate perspective, front and side views of the keel portion (side wall) of the saw blade of FIG. 2.

FIG. 5A illustrates the side wall 40a with a keel shape (having a keel-shape configuration), center 41a, periphery 49a, inner surface 42a and opposing outer surface 43a. The side wall includes teeth 46a on the distal end, on the periphery 49a. Additionally, teeth 44a are arranged on the inner surface 42a of the side wall 40a. The teeth 44a on the inner surface of the side wall 40a are partially cut out and bent inward. The teeth 44a may be arranged in a pattern on the sidewall 40a. Teeth 44a are preferably disposed in a row about parallel to the row formed by teeth 46a. Teeth 44a are spaced from teeth 46a by a distance "D" (FIG. 5B) representing the distance between teeth in the rows (i.e., the distance between the tooth support 45 of one of the teeth 44a and the tooth support 47 of the corresponding tooth from teeth 46a). The opposing side wall 40b illustrated in FIGS. 6A-C, may have teeth 44b arranged in a similar pattern, or in a different pattern on the sidewall 40b.

Figure 5B:
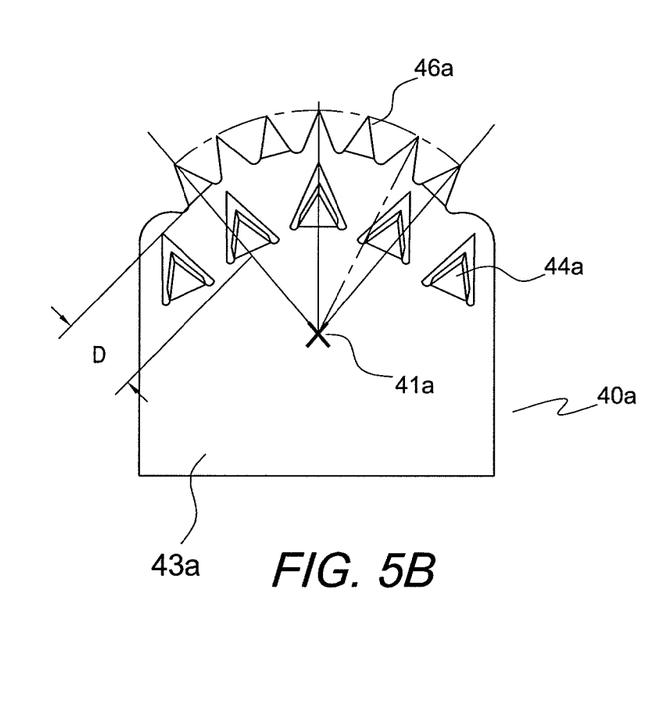
Figure 5C:
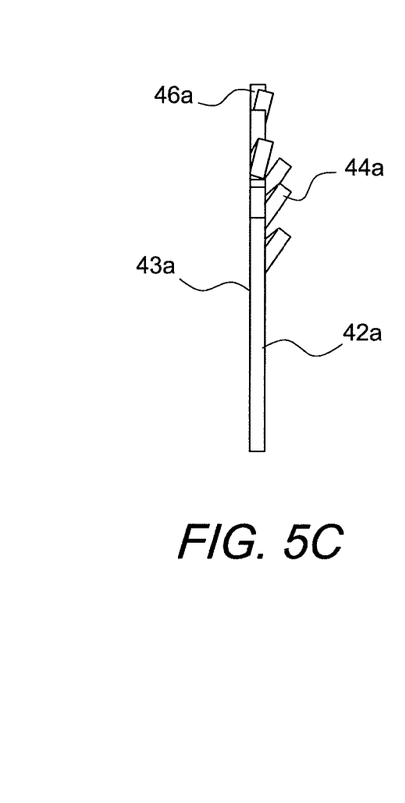
Figure 5D:
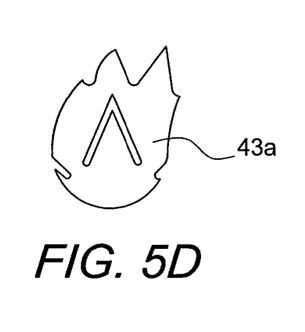
FIG. 5D is an enlarged view of a tooth of the keel portion of FIGS. 5A-C.

Referring to FIGS. 5A-C, the arrangement of the teeth 46a along the distal end of the sidewall 40a is now described. Each tooth 46a in the illustrated version of the invention is in the form of a triangle. Each tooth 46a is formed to have a most distal end tip (a point) and an opposite tooth support. End tips of teeth 46a extend away from the most distal end of the sidewall 40a. The teeth 46a may be alternating such that every other one is bent at an angle towards the inner surface 42a of the sidewall. This is referred to as the kerf, the spacing between the teeth provides for cutting and removing of bone debris. In an exemplary embodiment the angle is approximately 15 degrees and may range from about 0 to about 20 degrees. There may be several teeth arranged along the distal end of the sidewall 40a. In a preferred embodiment there are seven teeth.

Also shown in the embodiment illustrated in FIGS. 5A-C, teeth 44a are triangular in shape and are partially cut out of the side wall 40a. Each tooth 44a is formed to have a most distal end tip (a point) and an opposite tooth support. In other embodiments, teeth 44a may have any shape such as round, half round, or rectangular. The teeth 44a are bent outward from the sidewall at an angle of approximately 36 degrees and may range from about 0 to about 40 degrees. The number of teeth 44a may vary from 2 to 10. The teeth may be arranged in a pattern similar to the arrangement of the teeth 46a at the distal end of the sidewall (i.e., in a row (or multiple rows) about parallel to the row of distal teeth 46a) or in a completely different pattern. In an exemplary embodiment only, the teeth 44a are positioned in a row (or multiple rows) about parallel to the row of distal teeth 46a. However, other teeth patterns shown in FIGS. 7A-B may include multiple rows of teeth on the inner surface or a V-shape pattern where the teeth are overlapping to improve efficiency of bone removal. In a preferred embodiment, the teeth 44a are arranged as close to the base of the teeth 46a as possible to provide for the cleanest cut (but with teeth 44a still extending radially closer to the center 41a of the keel or side wall 40a than teeth 46a).

Figure 6A:
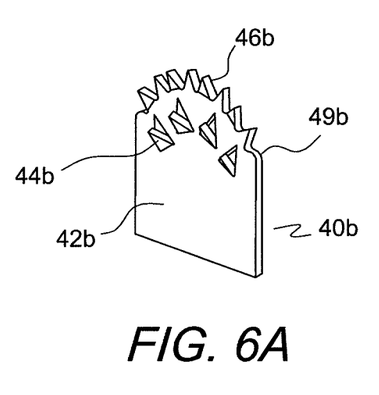
FIGS. 6A-C illustrate perspective, front and side views of the opposing keel portion (opposing side wall) of the saw blade of FIG. 2.
Figure 6B:
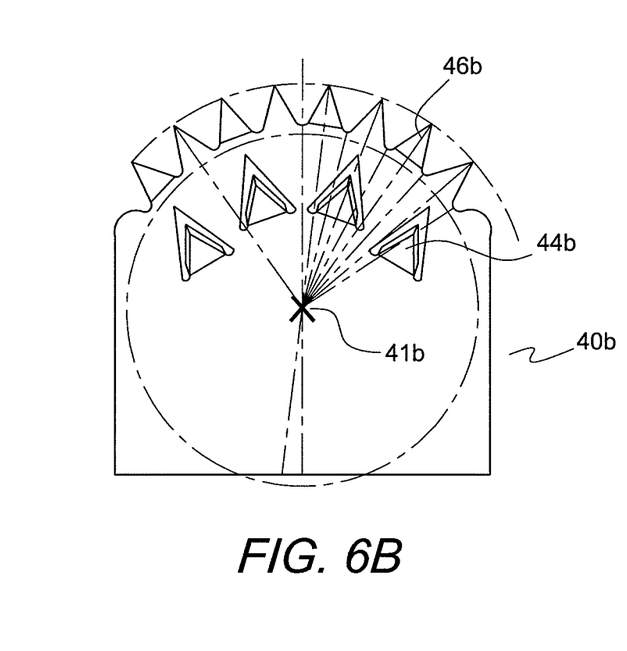
Figure 6C:
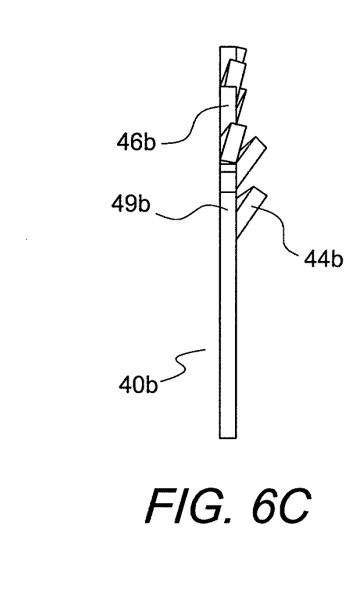
Figure 6D:
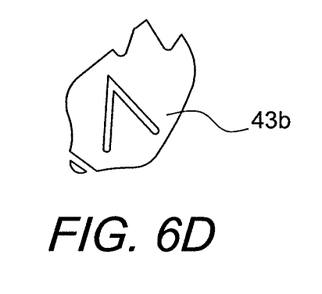
FIG. 6D is an enlarged view of a tooth of the opposing keel portion of FIGS. 5A-C.

Referring to FIGS. 6A-C, the arrangement of the teeth 46b along the distal end of the opposing sidewall 40b is now described. Each tooth 46b is formed in a triangle shape having a point at the most distal end tip and a tooth support (opposite to the end point tip). The teeth may be alternating such that every other one is bent at an angle towards the inner surface 42b of the sidewall 40b. In an exemplary embodiment, the angle is approximately 15 degrees and may range from about 0 to about 20 degrees. There may be several teeth arranged along the distal end of the sidewall 40b. In a preferred embodiment there are eight teeth.

The teeth 46a, 46b are arranged so that, on each sidewall, each tooth tip lies on the same curve. Although every other tooth is angled inward, each tip remains on the same curve. The inward angle provides for more aggressive removal of bone between the cuts created by the teeth 46a, 46b on the distal end of the two sidewalls. Teeth 44a, 44b extend radially closer to the center 41a, 41b of the keel or side wall 40a, 40b than teeth 46a, 46b. A section of bone remains between the two cuts created by the distal teeth 46a, 46b, which is removed by the teeth 44a, 44b on the inner surface 42a, 42b of the sidewall 40a, 40b to create a clean slot 200 that requires only minimal additional bone removal at the bottom of the slot by the surgeon.

Figure 7:
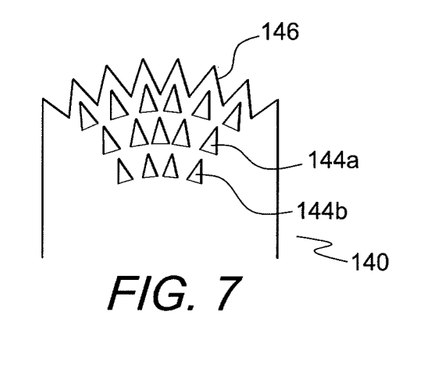
FIG. 7 illustrates an alternate embodiment of a side wall of the present invention (with multiple rows of teeth)

In an alternate embodiment illustrated in FIG. 7, side wall 140 may have multiple rows of teeth 144a, 144b arranged below the distal teeth 146 in varying numbers. The exemplary embodiment shown in FIG. 7 illustrates rows of teeth 144a, 144b about parallel to each other and parallel to the distal teeth 146 but the invention contemplates any numbers of rows of teeth 144 (such as rows 144a, 144b, etc) that are parallel or non-parallel to each other and/or to the distal teeth 146.

Figure 8A:
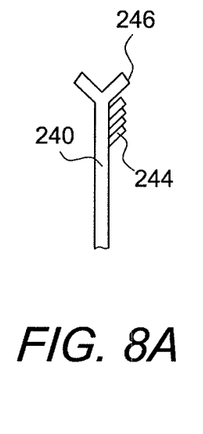
FIG. 8A illustrates a side view of another side wall of the present invention (with overlapping teeth for improved cutting efficiency)
Figure 8B:
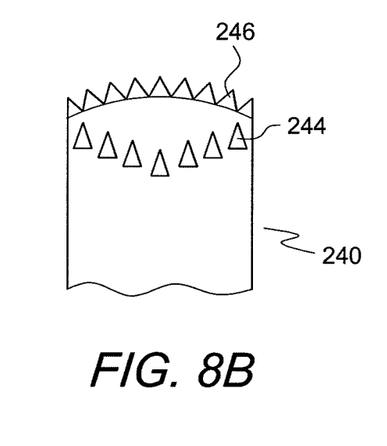
FIG. 8B illustrates a front view of the side wall of FIG. 8A.

Another embodiment of the side wall 240 is shown in FIGS. 8A and 8B. Side wall 240 has overlapping teeth 244 arranged below the distal teeth 246. The pattern is like a V (with a "V"-shaped configuration) such that the teeth on the opposing sides of the V create an overlap when they cut.

Figure 9:
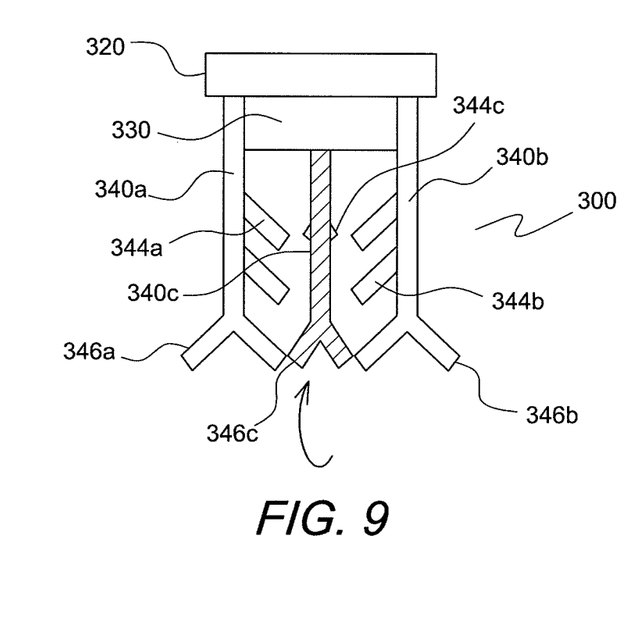
FIG. 9 illustrates a side view of another embodiment of a saw blade of the present invention (with a third blade positioned between first and second blades, so their kerfs overlap).

In a further embodiment of saw blade 300 of the present invention illustrated in FIG. 9, a third side wall 340c is added to the blade assembly, i.e., a third side wall 340c is positioned between first and second blades 340a, 340b so that their kerfs overlap. The third side wall 340c has distal teeth 346c and teeth 344c arranged on both sides of the surface of the side wall. In this embodiment, the kerfs created by each side wall overlap.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A cutting saw for removing bone or cartilage to form a slot in bone or cartilage, comprising:
a base having an oblong shape, a top surface and a bottom surface;
a first cutting saw blade and a second cutting saw blade, the first and second cutting saw blades extending from the bottom surface of the base and in a direction parallel to each other, wherein each of the first and second cutting saw blades is provided with a first plurality of teeth extending in a first direction and a second plurality of bent teeth extending in a second direction which is different from the first direction, the second plurality of bent teeth being bent at an inward angle towards an inner surface of a sidewall of each of the first and second cutting saw blades, and the second plurality of bent teeth of the first cutting saw blade being offset from the second plurality of bent teeth of the second cutting saw blade to create interlocking between the first and second cutting saw blades and to remove bone or cartilage between cuts created by the first plurality of teeth of the first and second cutting saw blades to form the slot, wherein the second plurality of teeth extend radially closer to the center of each blade than the first plurality of teeth, wherein the first plurality of teeth are disposed about a periphery of each of the first and second blades and extend forward from a most distal end of the blade, and the second plurality of teeth are disposed on the inner surface of the blade and form the inward angle with each of the first and second cutting saw blades, and wherein the first plurality of teeth are disposed in a first row, and the second plurality of teeth are disposed in a second row, the first row being parallel to the second row, wherein teeth of the first plurality of teeth of each of the first and second cutting saw blades are alternating so that every other tooth of the first plurality of teeth is bent at another angle towards the inner surface of the blade; and a spacer extending from the bottom surface of the base and provided between the first and second cutting saw blades, the spacer having a width equal to the width of the slot formed in the bone or the cartilage.

2. The cutting saw of claim 1, wherein the another angle is 0 to 20 degrees.

3. The cutting saw of claim 1, wherein the second plurality of teeth are disposed in a pattern.

4. The cutting saw of claim 1, wherein the second plurality of teeth have a triangular, round, half round, or rectangular configuration.

5. The cutting saw of claim 1, wherein the angle is 0 to 40 degrees.

6. The cutting saw of claim 1, wherein the second plurality of teeth are arranged in a series of multiple parallels rows of teeth.

7. The cutting saw of claim 1 further comprising a third cutting saw blade extending from the base and positioned between the first cutting saw blade and the second cutting saw blade.

8. The cutting saw of claim 7, wherein the third cutting saw blade is provided with a first plurality of teeth and a second plurality of teeth provided on each lateral side of the third cutting saw blade so that kerfs of the first and second plurality of teeth of each of the first, second and third cutting saw blades overlap.

9. A saw blade for cutting bone or cartilage, comprising:
a blade body having a center, a periphery, a first surface and an opposing second surface, the blade body having a keel-shape configuration;
a first plurality of distal teeth disposed about the periphery of the blade body; and
a second plurality of teeth disposed on the first surface of the blade body and forming an angle with the blade body, the first plurality of teeth extending radially further from the center of the blade body than the second plurality of teeth,
wherein every other tooth of the first plurality of distal teeth is bent and forms an angle with the first surface, and wherein the second plurality of teeth are arranged in a series of multiple parallel rows of teeth on the first surface forming a V-shaped pattern so that teeth on the opposing sides of the V create an overlap when they cut.

10. The saw blade of claim 9, wherein the angle is 36 degrees.

11. The saw blade of claim 9, wherein the second plurality of teeth have a triangular configuration and are partially cut out and bent inward.

12. The saw blade of claim 9, wherein the angle is 15 degrees.

13. The saw blade of claim 9, wherein tips of the first plurality of distal teeth are all situated on the same curve.

14. A saw blade for cutting bone or cartilage, comprising:
a body having a keel-shape configuration;
a first plurality of teeth arranged in a first row on the keel-shaped body, each of the plurality of first teeth having a cutting tip directed away from an end of the body; and
a second plurality of teeth arranged in a second row on the keel shaped body, each of the plurality of second teeth having a cutting tip directed toward the end of the body and toward the first plurality of teeth,
wherein teeth of the first plurality of teeth are alternating so that every other tooth of the first plurality of teeth is bent and forms an angle with a side surface of the body, and wherein the first plurality of teeth are disposed about the periphery of the body and extending forward from the end of the body, and wherein the second plurality of teeth are disposed on the side surface of the body and forming an angle with the body, the second plurality of teeth extending radially closer toward a center of the body than the first plurality of teeth, and wherein the first row is parallel to the second row.

15. The saw blade of claim 14, wherein the angle is 36 degrees.

16. A method of cutting bone to form a slot in the bone for providing an implant in the slot, comprising the steps of:
providing a cutting saw comprising a base having an oblong shape, a top surface and a bottom surface, and first and second cutting saw blades extending from the bottom surface of the base and in a direction parallel to each other, wherein each of the first and second cutting saw blades is provided with a body, a first plurality of distal teeth disposed about the periphery of the body and arranged in a first row on the body of each blade, and a second plurality of bent teeth disposed on a side surface of the body and forming an angle with the body and arranged in a second row on the body of each blade, the second row being parallel to the first row, the first plurality of distal teeth extending radially further from a center of the body than the second plurality of bent teeth, the second plurality of bent teeth of the first cutting saw blade being offset from the second plurality of bent teeth of the second cutting saw blade to create interlocking between the first and second cutting saw blades and to remove bone between cuts created by the first plurality of distal teeth of the first and second cutting saw blades, wherein the cutting saw further comprises a spacer extending from the bottom surface of the base and provided between the first and second cutting saw blades, the spacer having a width equal to the width of the slot formed in the bone; and
cutting bone with the saw blade by providing an initial cut with the distal teeth and removing additional material along a pathway of the initial cut with the second plurality of bent teeth to form the slot in the bone, so that, during a single cutting motion, the distal teeth provide the initial cut and the bent teeth remove the additional material along the pathway of the initial cut to form the slot in the bone.

17. The method of claim 16, wherein the cutting saw is further provided with a third cutting saw blade extending from the base and positioned between the first cutting saw blade and the second cutting saw blade.

18. The method of claim 17, wherein the third cutting saw blade is provided with a first plurality of distal teeth and a second plurality of bent teeth provided on each lateral side of the third cutting saw blade so that the kerfs of the first and second plurality of teeth of each of the first, second and third cutting saw blades overlap.

* * * * *